United States Patent
Sun et al.

(10) Patent No.: US 6,230,055 B1
(45) Date of Patent: May 8, 2001

(54) METHOD AND APPARATUS FOR ADAPTIVE TACHYCARDIA AND FIBRILLATION DISCRIMINATION

(75) Inventors: Weimin Sun, Plymouth; Martin Tze, Maplewood; Bruce H. KenKnight, Maple Grove; Yatheendhar Manicka, Woodbury, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/378,591

(22) Filed: Aug. 20, 1999

(51) Int. Cl.⁷ ....................................................... A61N 1/37
(52) U.S. Cl. ........................................................... 607/5
(58) Field of Search ................................. 607/4, 5, 6, 7, 607/8, 14

(56) References Cited

U.S. PATENT DOCUMENTS

| | | | |
|---|---|---|---|
| 4,202,340 | 5/1980 | Langer et al. | 128/419 |
| 5,193,535 | 3/1993 | Bardy et al. | 128/419 D |
| 5,193,550 | 3/1993 | Duffin | 129/697 |
| 5,205,283 | 4/1993 | Olson | 128/419 PG |
| 5,257,621 | 11/1993 | Bardy et al. | 607/5 |
| 5,311,874 | 5/1994 | Baumann et al. | 128/705 |
| 5,330,508 | 7/1994 | Gunderson | 607/14 |
| 5,342,402 | 8/1994 | Olson et al. | 607/5 |
| 5,354,316 | 10/1994 | Keimel | 607/15 |
| 5,366,486 | 11/1994 | Zipes et al. | 607/5 |
| 5,370,667 | 12/1994 | Alt | 607/19 |
| 5,379,776 | 1/1995 | Murphy et al. | 128/705 |
| 5,403,352 | 4/1995 | Rossing | 607/4 |
| 5,458,622 | 10/1995 | Alt | 607/15 |
| 5,857,977 | 1/1999 | Caswell et al. | 600/518 |
| 5,868,793 | 2/1999 | Nitzsche et al. | 607/5 |
| 5,873,897 | 2/1999 | Armstrong et al. | 607/14 |
| 5,891,170 | 4/1999 | Nitzsche et al. | 607/4 |
| 5,978,700 | 11/1999 | Nigam et al. | 600/518 |

FOREIGN PATENT DOCUMENTS

| | | | |
|---|---|---|---|
| 0684011 | 5/1995 | (EP) | A61B/5/0464 |
| 0744190 | 5/1996 | (EP) | A61N/1/365 |

OTHER PUBLICATIONS

Olson, W., "Safety Margins for Sensing and Detection: Programming Tradeoffs", *Implantable Cardioverter Defibrillator Therapy. The Engineering Clinical Interface* (*Developments in Cardiovascular Medicine, 188*) By Mark W. Kroll & Michael H. Lehmann, Shepard & Epstein, 388–420, (1996).

*Primary Examiner*—Scott M. Getzow
(74) *Attorney, Agent, or Firm*—Schwegman, Lundberg, Woessner & Kluth, P.A.

(57) ABSTRACT

An implantable cardioverter/defibrillator with antitachycardia pacing capability and method for operating same in which the detection zone boundary used to discriminate between tachycardia and fibrillation is adaptively adjusted based upon operating experience. Rate zones are provided for further classifying detected episodes of tachycardia and fibrillation according to the certainty of their being correctly identified based upon past operating experience. Adjustments of the rate zones and the fibrillation detection zone boundary are made based upon the results of antitachycardia pacing in attempting to terminate arrhythmic episodes.

20 Claims, 3 Drawing Sheets

METHOD AND APPARATUS FOR ADAPTIVE TACHYCARDIA AND FIBRILLATION DISCRIMINATION

FIELD OF THE INVENTION

This invention pertains to methods and systems for operating an implantable cardioverter/defibrillator with antitachycardia pacing capabilty. In particular, the invention relates to methods and systems for discriminating between tachycardia and fibrillation and the application of appropriate therapy thereto.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia, and atrial fibrillation. The most dangerous tachyarrythmias, however, are ventricular tachycardia (VT) and ventricular fibrillation (VF). Ventricular rhythms occur when an excitatory focus in the ventricle usurps control of the heart rate from the sinoatrial node. The result is rapid and irregular contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus directly into the myocardium. Ventricular tachycardia is characterized by distorted QRS complexes occurring at a rapid rate, while ventricular fibrillation is diagnosed when the ventricle depolarizes in a chaotic fashion with no recognizable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachycardias, including SVT's, VT, and VF. The electric shock terminates the tachycardia by depolarizing all excitable myocardium which prolongs refractoriness, interrupts reentrant circuits, discharges excitatory foci. Implantable cardioverter/defibrillators (ICD's) provide this kind of therapy by delivering a shock pulse to the heart when fibrillation is detected by the device.

Another type of electrical therapy for tachycardia is antitachycardia pacing (ATP). In ATP, the heart is competitively paced with one or more pacing pulses in an effort to interrupt reentrant circuits causing the tachycardia. Modem ICD's have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in some patient discomfort owing to the high voltage of the shock pulses. It is desirable, therefore, for the ICD to use ATP to terminate a tachyarrhythmia whenever possible. Generally, only cardioversion/defibrillation will terminate fibrillation and certain high rate tachycardias, while ATP can be used to treat lower rate tachycardias.

In current ICD's with ATP capability, ventricular fibrillation (VF) is distinguished from ventricular tachycardia (VT) using rate based criteria so that ATP or shock therapy can be delivered as appropriate. The heart rate is usually measured by detection of the time between successive R waves (i.e., ventricular depolarizations). A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as a fibrillation.

A commonly cited figure of merit is that for a patient with a normal sinus rhythm of 70 bpm, a rate of 150 bpm is considered tachycardia and a rate of over 210 bpm, fibrillation. Normally, the ICD is programmed with a fixed tachycardia detection zone boundary (i.e., the TDR) for detection of a tachyarrhythmia, and a fixed fibrillation detection zone boundary (i.e., the FDR) to distinguish VT from VE. Making the fibrillation detection zone boundary fixed, however, has several disadvantages. First, the heart rate that constitutes fibrillation is very different from patient to patient, making it difficult to set an appropriate value at the outset. Detection zone boundaries can be determined for an individual patient by a procedure in which arrhythmias are purposely induced and then characterized based upon their rate, EKG waveforms, and response to treatment. The rate of VF and VT when induced, however, may be quite different from spontaneously occurring VT and VF. Furthermore, only a limited number of induced episodes are available to guide the programming of the detection zone boundaries, thus necessitating a larger safety margin to avoid undersensing of fibrillation because of the uncertainty as to what the true zone boundary should be. Also, certain patients may suffer from ventricular tachycardia and ventricular fibrillation which have a range of rates that overlap, making it difficult to distinguish in a single instance low rate fibrillation from high rate tachycardia. Finally, the rate which separates tachycardia from fibrillation may change over time in a given patient due to, for example, progression of a disease process or the pharmacological effects of medications.

Most ICD's activate an.electronic timer when a tachyarrhythmia is detected. If the measured heart rate is low enough that the arrhythmia is characterized as a tachycardia, ATP therapy may be delivered. Upon expiration of the timer, however, if the arrhythmia is not terminated, a shock pulse is delivered. Setting the fibrillation detection zone boundaryat an inappropriate value thus results in delayed application of a necessary defibrillation pulse if it is too high, while setting the rate too low results in needless pain being inflicted on the patient as well as wastage of limited battery power.

SUMMARY OF THE INVENTION

The present invention is embodied by an implantable cardioverter/defibrillator device with antitachycardia pacing capability and method for operating same in which the detection zone boundary used to discriminate between tachycardia and fibrillation is adaptively adjusted based upon therapy outcomes detected by the device. In accordance with the invention, a cardiac arrhythmia is detected by measuring the heart rate and determining whether it exceeds a selected arrhythmia threshold value. The arrhythmia is classified as a tachycardia or a fibrillation according to whether the heart rate is below or above, respectively, a selected fibrillation rate boundary. If the arrhythmia is classified as a tachycardia, antitachycardia pacing therapy is delivered. If the antitachycardia pacing fails to terminate the arrhythmia, the fibrillation detection zone boundary is decreased. A boundary zone extending above and below the fibrillation detection zone boundary may further be provided such that if a detected tachycardia falls within the boundary zone, a successful antitachycardia pace results in the fibrillation detection zone boundary being increased so that the lower limit of the boundary zone is equal to the measured heart rate, while a failure causes the fibrillation detection zone boundary to be decreased to the measured heart rate. Failure to terminate non-boundary zone tachycardia results in the fibrillation detection zone boundary being decreased by a selected amount. If fibrillation is detected within the boundary zone, antitachycardia pacing is delivered and, if successful, results in the fibrillation detection zone boundary being increased to the measured heart rate. Failure of the antitachycardia pacing causes the fibrillation detection zone boundary to be moved down such that the upper limit of the boundary zone is equal to the measured heart rate. A soft zone defined by a lower limit equal to the upper limit of the boundary zone and a selected upper limit may further be provided. If a tachyarrhythmia is detected within the soft zone, antitachycardia pacing is delivered and, if successful in terminating the arrhythmia, causes the fibrillation detection zone boundary to be increased by a selected amount. If the tachyarrhythmia is not terminated by the trial of antitachycardia pacing, the fibrillation detection zone boundary is left unchanged, and the upper limit of the soft zone is decreased by a selected amount. The values of the fibrillation detection zone boundary, the boundary zone limits, and the soft zone limits may be made to vary in accordance with measured heart rate stability to further aid in discrimination between tachycardia and fibrillation.

DESCRIPTION OF A SPECIFIC EMBODIMENT

In the description that follows, a microprocessor-based ICD will be referred to as incorporating the system and method that is the present invention. In the embodiment to be described, the invention is implemented with programmed instructions in memory executed by a microprocessor. It should be appreciated, however, that certain functions of an ICD can be controlled by custom logic circuitry either in addition to or instead of a programmed microprocessor. The term "circuitry" as used herein should therefore be taken to mean either custom circuitry (i.e., dedicated hardware) or a microprocessor executing programmed instructions contained in a processor-readable storage medium along with associated circuit elements.

Figure 1:
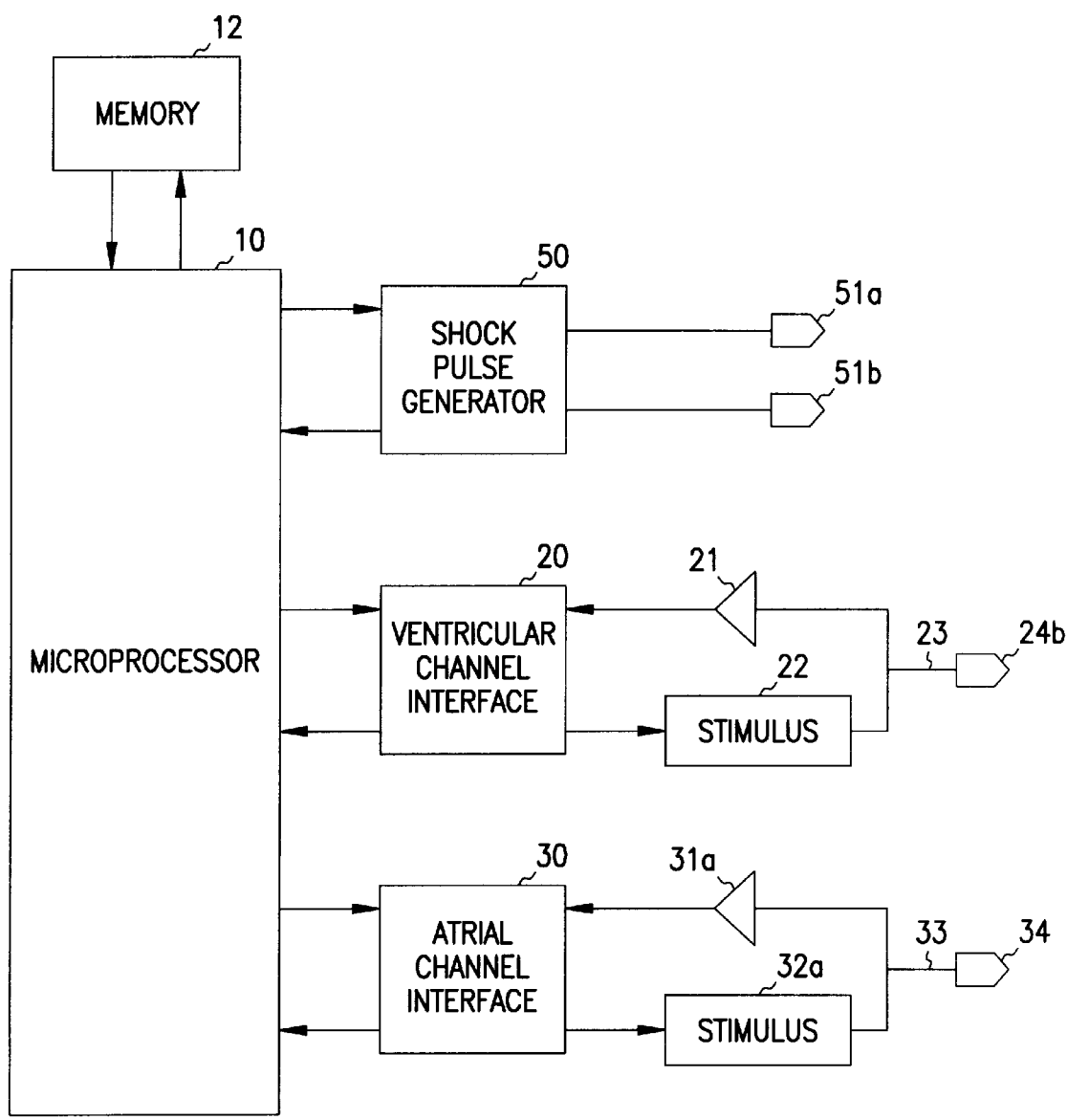
FIG. 1 is a system diagram of a microprocessor-based implantable cardioverter/defibrillator with antitachycardia pacing capabilty.

FIG. 1 is a system diagram of a microprocessor-based implantable cardioverter/defibrillator with the capability of also delivering antitachycardia pacing therapy. A microprocessor 10 communicates with a memory 12 via a bidirectional data bus. The memory 12 typically comprises a ROM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used in conjunction with antitachycardia pacing and for measuring heart rate in order to detect tachycardia and fibrillation. A shock pulse generator 50 is also interfaced to the microprocessor for delivering cardioversion or defibrillation pulses to the heart via a pair of electrodes 51a and 51b.

The ICD detects a ventricular tachyarrhythmia by measuring a heart rate via the ventricular sensing channel and determining whether the rate exceeds a selected threshold value. Once a tachyarrhythmia is detected, the rhythm is further classified into either a tachycardia or a fibrillation by comparing the heart rate to a fibrillation rate boundary. FIGS. 2A through 2D are graphs of measured heart rate HR, showing the ventricular tachyarrythmia threshold rate TDR (i.e., the tachycardia detection rate) and the fibrillation detection zone boundary FDR (i.e., the fibrillation detection rate). Rates above the TDR and below the FDR are classified as ventricular tachycardia, while those above the fibrillation detection zone boundary are classified as ventricular fibrillation. Two zones are also provided to further classify the detected arrhythmia and provide for adaptive adjustment of the fibrillation detection zone boundary in accordance with the invention. A boundary zone BZ is a range of heart rates above and below the fibrillation detection zone boundary which is defined by a selected upper limit UL and lower limit LL on either side of the rate boundary. The UL and LL may be, for example, 90% and 110% of the fibrillation rate boundary. A soft zone SZ is a range of heart rates above the upper limit of the boundary zone BZ and below a selected soft zone limit SZL. The soft zone limit may be chosen to be, for example, 125% of the fibrillation rate boundary.

Figure 2A:
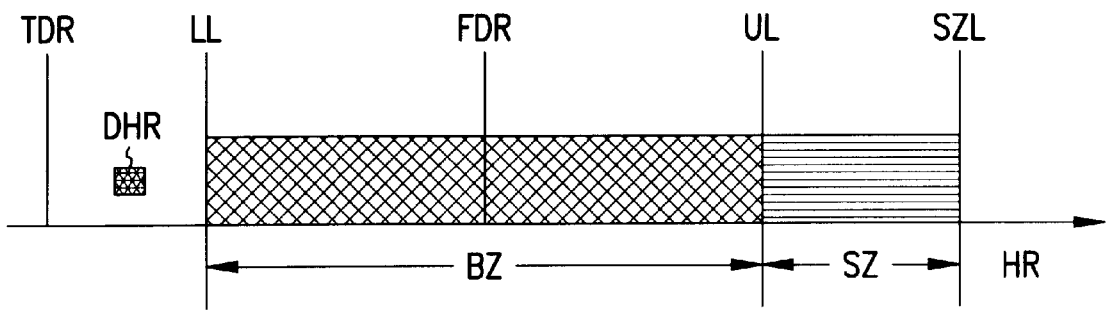
FIGS. 2A through 2D are graphs showing the fibrillation detection zone boundary, boundary zone, and soft zone.

To illustrate how an ICD may operate in accordance with the invention, four cases will be considered with reference to FIGS. 2A through 2D. First, consider a detected heart rate DHR above the tachyarrhythmia threshold but below the lower limit LL of the boundary zone as depicted in FIG. 2A. The tachyarrhythmia is thus classified as a tachycardia, and antitachycardia pacing is delivered. If the tachycardia is terminated, no change is made to the rate boundary. On the other hand, if the tachycardia persists after the antitachycardia pacing, the fibrillation detection zone boundary FDR is decreased by a selected amount. This reflects lessened certainty that the tachyarrhythmia is actually a tachycardia and not fibrillation. This procedure is then repeated until either the tachycardia is terminated, the measured heart rate falls within one of the zones as described below, or a selected time interval expires in which case a shock pulse is delivered to stop the tachycardia.

Figure 2B:
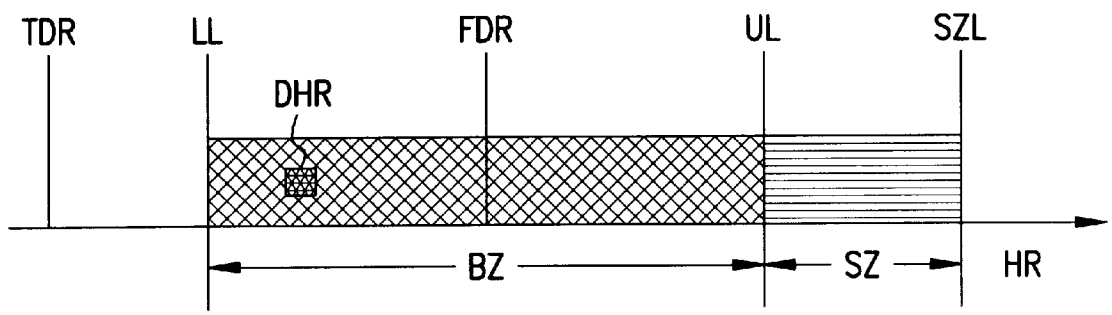

Shown in FIG. 2B is the situation where the detected heart rate DHR is a tachycardia below the fibrillation detection zone boundary but within the boundary zone BZ. Accordingly, antitachycardia pacing is delivered. In this situation, however, successful termination of the tachycardia results in the fibrillation detection zone boundary being increased such that the lower limit LL is equal to the measured heart rate because it is now more certain that the tachycardia has been correctly classified. Failure of the antitachycardia pacing to restore normal rhythm causes the fibrillation detection zone boundary to be decreased to the measured heart rate. The information provided by the failed antitachycardia pacing means that the probability of the measured heart rate being a fibrillation instead of a tachycardia is increased.

Figure 2C:
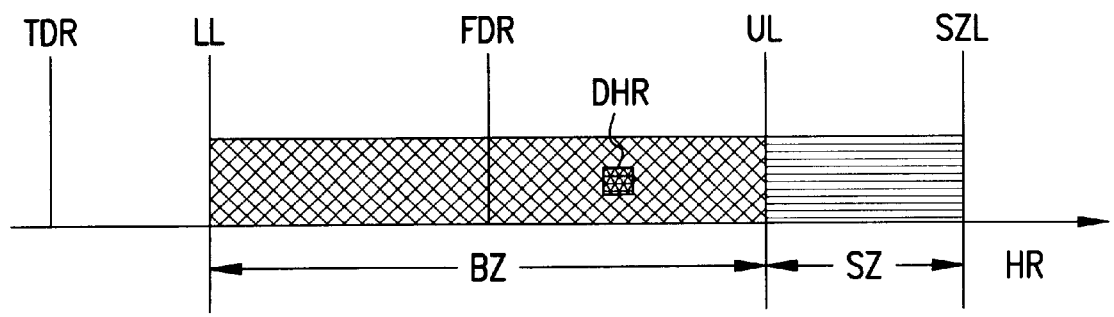

A tachyarrhythmia with a detected heart rate DHR above the soft zone SZ, as shown in FIG. 2C, is classified as a fibrillation, and a cardioversion or defibrillation pulse is delivered to the heart. If the fibrillation is below the upper limit UL of the boundary zone, however, a trial of antitachycardia pacing is attempted to ascertain whether it may actually be a tachycardia. The trial may take place during the charging period of the cardioverter/defibrillator shocking capacitor. If the antitachycardia pacing succeeds, the fibrillation detection zone boundary is increased to the measured heart rate so that subsequent measured heart rates at that value will be classified as tachycardias. If the fibrillation persists, the fibrillation detection zone boundary is decreased such that the upper limit UL becomes equal to the measured heart rate. This reflects the increased certainty that the measured heart rate is a fibrillation in view of the failed trial of antitachycardia pacing.

Figure 2D:
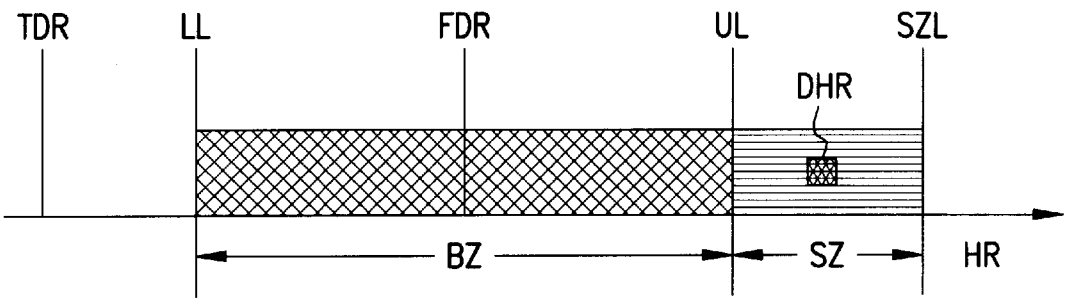

A tachyarrhythiia is in the soft zone SZ if the detected heart rate DHR is above the upper limit UL of the boundary zone but below the soft zone limit SZL, as depicted in FIG. 2D. In this case, antitachycardia pacing is again tried first as in the case of a boundary zone fibrillation to allow for the possibility that the fibrillation detection zone boundary is set too high. If the antitachycardia pacing is successful in ending the tachyarrhythmia in this situation, however, the fibrillation detection zone boundary is only increased by a selected amount and not adjusted to equal the measured heart rate. This reflects the fact that although the antitachycardia pacing was successful in this instance in terminating a tachyarrhythmia having the measured heart rate, past experience indicates that there is less certainty that subsequent tachyarrhythmias with the measured heart rate will be tachycardias terminable by antitachycardia pacing. Should the antitachycardia pacing fail to convert the tachyarrhythmia to normal rhythm, the upper limit of the soft zone SZL is decreased by a selected amount. This reflects the increased certainty that a fibrillation with the measured is actually a fibrillation. No adjustment is made to the fibrillation rate boundary, however, since the tachyarrhythmia was correctly classified as a fibrillation, and the failed trial of antitachycardia pacing provides no information as to what heart rate constitutes a tachycardia.

Figure 3:
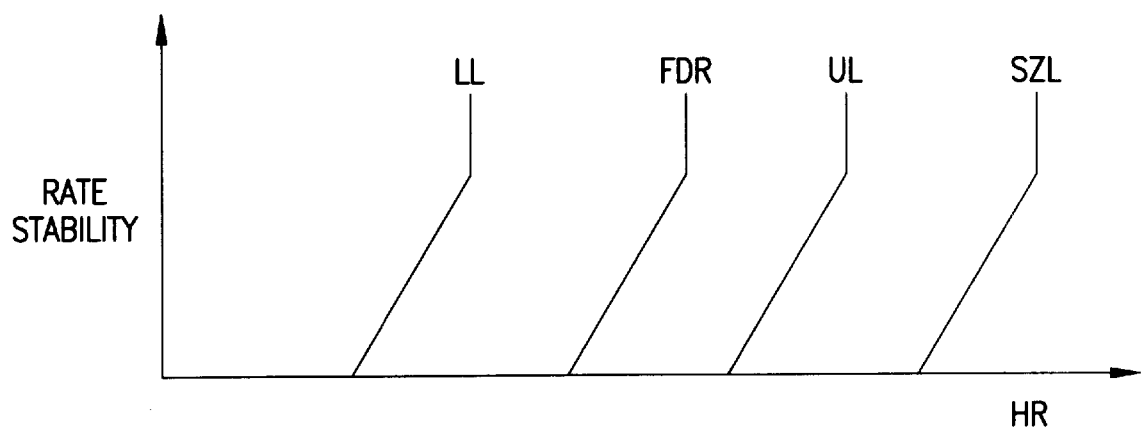
FIG. 3 is a graph showing how the fibrillation rate boundary, boundary zone, and soft zone may be varied with heart rate stability.

Another parameter which can be used to aid in discriminating between tachycardia and fibrillation is heart rate variability or its inverse, heart rate stability. Ventricular fibrillation is characterized by chaotic depolarizations of the myocardium resulting in increased irregularity of the measured heart rate. For a given heart rate, therefore, the lower the heart rate stability, the more probable it is that the heart rate represents ventricular fibrillation and not tachycardia. To take advantage of this information, heart rate stability can be measured by the ICD and used to vary the values of the fibrillation detection zone boundary FDR, the upper and lower limits of the boundary zone UL and LL, and the upper limit of the soft zone SZL. FIG. 3 shows how those values can be made to increase with heart rate stability to indicate the increased probability that a given heart rate is a tachycardia. An upper stability limit is provided at which the values do not vary further so that very high heart rates will be regarded as fibrillation regardless of the rate stability. Although FIG. 3 shows the fibrillation detection zone boundary and rate zone limit values varying linearly with rate stability, other embodiments may use a different functional relationship that maintains a positive correlation between the values and heart rate stability.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating an implantable cardioverter/defibrillator with antitachycardia pacing capability, comprising:

detecting a cardiac arrhythmia by measuring a heart rate and determining the rate to be above a selected arrhythmia threshold value;

classifying the arrhythmia as a tachycardia or a fibrillation according to whether the heart rate is below or above, respectively, a selected fibrillation detection zone boundary, delivering antitachycardia pacing therapy if the arrhythmia is classified as a tachycardia; and, decreasing the fibrillation detection zone boundary if the antitachycardia pacing fails to terminate an arrhythmia classified as a tachycardia.

2. The method of claim 1 further comprising:

further classifying the arrhythmia according to whether the arrhythmia is within a boundary zone defined as a selected range of heart rates with upper and lower limits above and below, respectively, the fibrillation rate boundary, wherein the arrhythmia is designated a boundary zone arrhythmia if the arrhythmia falls within the boundary zone; and, increasing the fibrillation detection zone boundary by an amount such that the lower limit of the boundary zone equals the measured heart rate if the antitachycardia pacing therapy is successful in terminating a boundary zone tachycardia.

3. The method of claim 2 further comprising:

decreasing the fibrillation detection zone boundary by a selected amount if the antitachycardia pacing fails to terminate a tachycardia not within the boundary zone; and, decreasing the fibrillation detection zone boundary by an amount such that the detection zone boundary equals the measured heart rate if the antitachycardia pacing therapy fails to terminate a boundary zone tachycardia.

4. The method of claim 3 further comprising:

delivering antitachycardia pacing therapy if the arrhythmia is classified as a boundary zone fibrillation;

increasing the fibrillation detection zone boundary by a selected amount if the antitachycardia pacing therapy is successful in terminating a boundary zone fibrillation; and, decreasing the fibrillation detection zone boundary by a selected amount if the antitachycardia pacing therapy fails to terminate a boundary zone fibrillation.

5. The method of claim 3 further comprising:

delivering antitachycardia pacing therapy if the arrhythmia is classified as a boundary zone fibrillation;

increasing the fibrillation detection zone boundary by an amount such that the detection zone boundary equals the measured heart rate if the antitachycardia pacing therapy is successful in terminating a boundary zone fibrillation.

6. The method of claim 5 further comprising decreasing the fibrillation detection zone boundary by an amount such that the upper limit of the boundary zone equals the measured heart rate if the antitachycardia pacing therapy fails to terminate a boundary zone tachycardia.

7. The method of claim 6 further comprising:

further classifying a fibrillation according to whether the fibrillation is within a soft zone defined as a selected range of heart rates with a selected upper limit and a lower limit equal to the upper limit of the boundary zone, wherein the fibrillation is designated a boundary zone fibrillation if the fibrillation falls within the soft zone;

delivering antitachycardia pacing therapy if the fibrillation is classified as a boundary zone fibrillation; and, increasing the fibrillation detection zone boundary by a selected amount if the antitachycardia pacing therapy is successful in terminating a soft zone fibrillation.

8. The method of claim 7 further comprising decreasing the upper limit of the soft zone by a selected amount if the antitachycardia pacing therapy fails to terminate a soft zone fibrillation.

9. The method of claim 8 wherein the values of the fibrillation rate boundary, the boundary zone upper and lower limits, and the soft zone upper limit are defined so as to be positively correlated with a measured heart rate stability value over a selected range of stability values.

10. The method of claim 8 wherein the values of the fibrillation rate boundary, the boundary zone upper and lower limits, and the soft zone upper limit are defined so as to vary in proportion to a measured heart rate stability value up to a selected upper limit.

11. The method of claim 8 further comprising delivering a shock pulse if the fibrillation has a measured heart rate above the soft zone upper limit.

12. An implantable cardioverter/defibrillator with antitachycardia pacing capability, comprising:

a sensing channel for measuring heart rate;

an antitachycardia pace generator;

a shock pulse generator, and, logic circuitry for implementing the method recited in claim 1.

13. The implantable cardioverter/defibrillator of claim 12 further comprising logic circuitry for implementing the method recited in claim 8.

14. The implantable cardioverter/defibrillator of claim 12 further comprising logic circuitry for implementing the method recited in claim 10.

15. A processor-readable storage medium having processor-executable instructions for performing the method recited in claim 1.

16. The processor-readable storage medium of claim 15 further having processor-executable instructions for performing the method recited in claim 2.

17. The processor-readable storage medium of claim 15 further having processor-executable instructions for performing the method recited in claim 5.

18. The processor-readable storage medium of claim 15 further having processor-executable instructions for performing the method recited in claim 6.

19. The processor-readable storage medium of claim 15 further having processor-executable instructions for performing the method recited in claim 8.

20. The processor-readable storage medium of claim 15 further having processor-executable instructions for performing the method recited in claim 10.

\* \* \* \* \*